United States Patent [19]

Gordon et al.

[11] Patent Number: 4,780,543
[45] Date of Patent: Oct. 25, 1988

[54] 1-PHENYL-3-(2-NITROETHENYL)PYRAZO-LINE AND 1-PHENYL-3-(2,2-DICYANOETHENYL)-PYRAZOLINE

[75] Inventors: Paul Gordon; Brian Bothwell, both of Rochdale, United Kingdom

[73] Assignee: Imperial Chemical Industries PLC, London, England

[21] Appl. No.: 98,996

[22] Filed: Sep. 21, 1987

[30] Foreign Application Priority Data

Oct. 7, 1986 [GB] United Kingdom ............ 8624020
Oct. 14, 1986 [GB] United Kingdom ............ 8624643

[51] Int. Cl.$^4$ .................................. C07D 231/06
[52] U.S. Cl. ............................ 548/379; 350/96.12
[58] Field of Search ................................ 548/379

[56] References Cited

U.S. PATENT DOCUMENTS 3,835,126 9/1974 Hengler et al. ............... 548/379
4,454,211 6/1984 Takasu et al. ............... 548/379

Primary Examiner—Mary C. Lee
Assistant Examiner—Kurt G. Briscoe
Attorney, Agent, or Firm—Cushman, Darby & Cushman

[57] ABSTRACT

A compound of the formula:

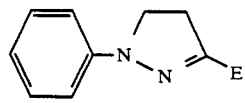

I wherein
E is an ethenyl group of the formula:

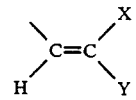

II in which
X is H when Y is $NO_2$;
Y is H when X is $NO_2$; or
X is CN when Y is CN which has the capacity to form a crystal in which the molecules are aligned substantially in the same manner giving it non-linear optical properties. The crystalline product is thus adapted for use in devices exhibiting non-linear optical effects.

3 Claims, No Drawings

1-PHENYL-3-(2-NITROETHENYL)PYRAZOLINE AND 1-PHENYL-3-(2,2-DICYANOETHENYL)PYRAZOLINE

This specification describes an invention relating to a substituted pyrazoline and especially to such a pyrazoline having non-linear optical (NLO) activity.

According to the present invention there is provided a compound of the formula:

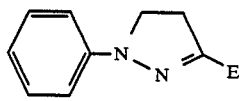   I wherein

E is an ethenyl group of the formula:

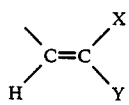   II in which

X is H when Y is $NO_2$;
Y is H when X is $NO_2$; or
X is CN when Y is CN.

1-phenyl-3-(2-nitroethenyl)-pyrazoline can be prepared by heating 3-formyl-1-phenyl-2-pyrazoline with nitromethane. The reaction is preferably performed at 80°–120° C. for from 30 minutes to 2 hours. The product may be purified by chromatography and/or recrystallisation.

1-phenyl-3-(2,2-dicyanoethenyl)-pyrazoline can be prepared by reacting 3-formyl-1-phenyl-2-pyrazoline with malonitrile preferably in the presence of a weak alkaline buffer such as sodium acetate, in a polar organic solvent such as an alkanol and with slight warming to complete the reaction. The product can be purified by chromatography and/or recrystallisation.

A molecule of the pyrazoline is non-centrosymmetric by virtue of its polarisation along an axis through the phenyl group, the pyrazoline ring and the ethenyl group, E. It can, therefore, be represented as a vector directed along this axis from the phenyl group towards the ethenyl group, E. An optical element comprising the pyrazoline, either alone or in conjunction with other substances, in which the molecules of the pyrazoline are "ordered" (i.e. not randomly oriented so that the sum of the individual molecular vectors is zero) will have an overall non-centrosymmetry and thus be adapted for second-order NLO applications.

In this specification the term "optical" is used to indicate properties associated with electromagnetic radiation in the region of the electromagnetic spectrum from wavelengths of 200 nanometres (nm) to 11,000 nm, especially 300 nm to 3000 nm, and is not limited to electro-magnetic radiation in the visible region of the spectrum.

According to a second aspect of the present invention there is provided a non-linear optical element, hereinafter referred to as an "NLO element" comprising, as the active species, a pyrazoline according to Formula I By the term NLO element is meant an element capable of transmitting an optical signal in such a manner that it can interact with the active species.

It has been found that the pyrazoline compound according to Formula I will form a crystal in which a substantial proportion of the molecules are aligned in an ordered manner so that the crystal itself is adapted for use as an NLO element.

The crystalline NLO element may comprise the pyrazoline alone or it may comprise a physical or chemical combination of the pyrazoline with other compounds which may or may not in themselves have NLO properties. The NLO element may be prepared by crystallisation from solution, from the melt, by vapour phase transport or by other known methods of crystallisation provided the process produces a crystal in which the molecules are "ordered".

Alternatively, the NLO element may comprise a chemically inert medium, such as a liquid crystal material, containing the pyrazoline, in which the pyrazoline may be ordered by the application of a dc electric field.

In another configuration, the NLO element may comprise a thin film comprising one or more ordered layers of the pyrazoline on a transparent or reflecting substrate, for use in waveguiding geometries well known in this field of work. The film may itself be used as a waveguide, to maximise NLO interactions, or may be used as a non-linear optically-active overcoat to an active or passive waveguide.

The film may be formed by any of the well-known methods for forming such films, such as, for example, by epitaxial crystal growth or by crystallisation of the material in a narrow cavity between two suitable transparent or reflecting substrates.

The NLO element may be employed in an optical device exhibiting a second-order NLO effect such as second harmonic generation, frequency mixing or the d.c. electro-optical effect.

Examples of non-linear optical effects using an NLO element in accordance with the present invention, in the form of a bulk crystalline sample, for example a single crystal, of the NLO compound, include:

(1) Second Harmonic Generation: A laser beam of given frequency, incident on one face of an NLO element comprising a single-crystal of the pyrazoline, at an angle parallel to the so-called "phase-matching" direction, causes the emission from the element of a coherent beam of laser radiation, at twice the frequency of the incident beam, in a direction substantially parallel to the incident beam.

(2) Electro-optical Amplitude Modulation. A polarised laser beam is directed so that it passes through a birefrequent NLO element, comprising a crystal of the pyrazoline, at an angle such that the output beam is elliptically polarised, the change in polarisation state being caused by the passage through the crystal. The beam next passes through a polarising medium (analyser) which transmits a proportion of the beam. An electric field applied across the NLO element causes a change in the birefringence of the element (the "dc electro-optic effect") and a consequent change in the polarisation state (ellipticity) of the output beam. This in turn changes the proportion of the beam transmitted by the analyser.

Where the substrate is transparent at the wavelength of incident radiation the element may be in the form of an optical waveguide having a layer of the pyrazoline on the outer surface. With this form of element an optical signal passing along the waveguide interacts with the superficial layer of the pyrazoline, via the evanescent wave which extends into this layer, giving rise to second-order NLO effects. Examples of suitable substances for a substrate in the form of a waveguide are glass, lithium niobate and silicon nitride on oxidised silicon.

Alternatively, a transparent substrate may be in the form of a plate or disc on one, or both, surfaces of which a crystalline layer of the pyrazoline can be formed, e.g. by crystal growth. With this form of element a second order NLO effect may be obtained by transverse illumination of the surface(s) carrying the pyrazoline layer. Suitable substrates for such an optical element include glass, silica and polymethylmethacrylate (PMMA).

Where the substrate is reflecting it conveniently has a plane reflecting surface on which a superficial crystalline layer of the pyrazoline may be formed so that the optical signal passes through the layer immediately before and after contact with the reflecting surface. A suitable reflecting substrate conveniently comprises a reflecting film of a metal such as aluminium, silver, aluminium or silver deposited on a support such as glass, silica, quartz or PMMA. With this form of optical element it is possible to attain efficient second-order non-linear processes by exciting the so called "surface plasmon" modes reported in the literature [Stegman et al, Appl.Phys.Lett. 41 (10) 906, 1982; Sand et al, Appl.Optics 21 (22) 3993, 1982].

The optical element of the second aspect of the present invention may be used in various known forms of optical device incorporating an optical element, by replacing the conventional NLO compound used therein, e.g. lithium niobate, with a pyrazoline of Formula I.

The invention is further illustrated by the following Examples in which all parts and percentages are by weight unless otherwise indicated.

EXAMPLE 1

1-phenyl-3-(2-nitroethenyl)-pyrazoline

A mixture of 3-formyl-1-phenyl-2-pyrazoline (3.48 g), n-butylamine (0.2 ml) and nitromethane (10 ml) was stirred at 100° C. for 1 hour, then was cooled to room temperature. The resultant dark red crystalline mass was dissolved in toluene and was eluted down a silica column with toluene. The major orange fraction was evaporated to dryness under reduced pressure and the residue was recrystallised from ethanol to give a 59% yield of dark red micro crystals (MP 150° C.).

EXAMPLE 2

1-phenyl-3-(2,2-dicyanoethenyl)-pyrazoline

A mixture of 3-formyl-1-phenyl-2-pyrazoline (1.74 g), malononitrile (0.66 g) and sodium acetate trihydrate (0.27 g) in ethanol (50 ml) was stirred together at room temperature to give an orange suspension. The mixture was warmed gently for 5 minutes to complete the reaction, cooled to room temperature and the solid product separated by filtration. The crude product was purified by chromatography (silica/dichloromethane) and recrystallisation from acetonitrile to give a 40% yield of tiny red needles (MP 194° C.). 3-Formyl-1-phenyl-2-pyrazoline was prepared by the method of U.S. Pat. No. 3,013,015, from 1-phenyl-2-pyrazoline, prepared by the method of Fischer and Knoevenagel (Annalen 239, 196 [1887]).

EXAMPLE 3

The product of Example 1 was examined for non-linear optical response by irradiation in the form of a powder with a 1.9 $\mu$m beam from a Raman-shifted Nd:YAG laser (cf 1.06 $\mu$m) using the method of Kurtz and Perry (J Appl Phys, 39, 3798 [1968]). The strength of the second harmonic generated by the product of Example 1 was measured as being 490 times greater than that generated by urea.

EXAMPLE 4

The product of Example 2 was examined for non-linear optical response using the same method and conditions as Example 3. The strength of the second harmonic generated by the product of Example 2 was measured as being 100 times greater than that generated by urea.

EXAMPLE 5

The product of Example 2 was examined for electro-optical amplitude modulation ("dc electro optic effect") as hereinbefore described and the reduced half wave voltage was found to be 300 volts.

We claim:

1. A compound of the formula:

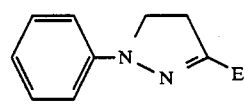

I wherein
E is an ethenyl group of the formula:

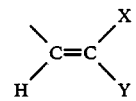

II in which
X is H and Y is $NO_2$;
Y is H and X is $NO_2$; or
X is CN and Y is CN.

2. A compound according to claim 1 wherein X is H and Y is $NO_2$.

3. A compound according to claim 1 wherein X and Y are both CN.

* * * * *